United States Patent [19]

Cochran et al.

[11] Patent Number: 5,172,005

[45] Date of Patent: Dec. 15, 1992

[54] ENGINEERED LIGHTING SYSTEM FOR TDI INSPECTION COMPRISING MEANS FOR CONTROLLING LIGHTING ELEMENTS IN ACCORDANCE WITH SPECIMEN DISPLACEMENT

[75] Inventors: Don W. Cochran, Highland Heights; James R. Austin, Mentor-on-the-Lake, both of Ohio

[73] Assignee: Pressco Technology, Inc., Solon, Ohio

[21] Appl. No.: 658,093

[22] Filed: Feb. 20, 1991

[51] Int. Cl.$^5$ .................... G01N 21/86; H04N 7/18
[52] U.S. Cl. ................................ 250/57; 356/430; 358/101
[58] Field of Search ............... 250/560, 561, 562, 572, 250/571, 234, 235, 236; 356/376, 379, 380, 386, 387, 430, 431, 434, 435; 358/101, 106

[56] References Cited

U.S. PATENT DOCUMENTS

| | | | |
|---|---|---|---|
| 3,222,524 | 12/1965 | Lee | 250/106 |
| 3,746,784 | 7/1973 | van Oosterhout | 178/6.8 |
| 3,903,416 | 9/1975 | Fox | 250/360 |
| 4,002,823 | 1/1977 | van Oosterhout | 358/106 |
| 4,141,566 | 3/1979 | Peyton et al. | 358/101 |
| 4,165,277 | 8/1979 | Frewin | 209/3.3 |
| 4,217,491 | 8/1980 | Dufford, Jr. et al. | 250/223 R |
| 4,256,957 | 3/1981 | Ford et al. | 250/223 B |
| 4,271,408 | 6/1981 | Teshima et al. | 340/702 |
| 4,293,219 | 10/1981 | Ducloux | 356/240 |
| 4,305,658 | 12/1981 | Yoshida | 356/23 |
| 4,318,808 | 3/1982 | Atkinson | 209/533 |
| 4,343,021 | 8/1982 | Frame | 358/213 |
| 4,344,146 | 8/1982 | Davis, Jr. et al. | 364/522 |
| 4,364,088 | 12/1982 | Kubota | 358/106 |
| 4,367,405 | 1/1983 | Ford | 250/223 |
| 4,380,025 | 4/1983 | Deane | 358/106 |
| 4,385,233 | 5/1983 | Lovalenti | 250/223 |
| 4,385,318 | 5/1983 | Miller | 358/106 |
| 4,427,800 | 1/1984 | Kanade et al. | 250/222.1 |
| 4,439,788 | 3/1984 | Frame | 358/213 |
| 4,442,455 | 4/1984 | Huignard et al. | 358/209 |
| 4,446,481 | 5/1984 | Edamatsu et al. | 358/106 |
| 4,486,776 | 12/1984 | Yoshida | 358/106 |
| 4,491,868 | 1/1985 | Berridge, Jr. et al. | 358/139 |
| 4,509,076 | 4/1985 | Yoshida | 358/106 |
| 4,530,036 | 7/1985 | Conti | 362/32 |
| 4,567,551 | 1/1986 | Choate | 362/398 |
| 4,581,632 | 4/1986 | Davis et al. | 358/106 |
| 4,586,080 | 4/1986 | Hoyt et al. | 358/106 |
| 4,595,289 | 6/1986 | Feldman et al. | 356/237 |

(List continued on next page.)

FOREIGN PATENT DOCUMENTS 341806  2/1989  European Pat. Off. .
336563  3/1989  European Pat. Off. .

OTHER PUBLICATIONS

L. Vargas et al., Solving the Photographic Negative Inspection Problem, Photonics Spectra, pp. 183-184, Jun. 1991.
A. Novini, "Fundamentals of Machine Vision Lighting", Penn Video Inc., copyright 1985.
Penn Video Inc., "Pulsar Machine Vision Strobes".
A. Novini, "Fundamentals of Machine Vision Component Selection", Penn Video Inc., copyright 1984.
Penn Video Inc., "Programmable Logic Controlled Vision".
A. Novini, "Fundamentals of Strobe Lighting for Machine Vision", Penn Video Inc., copyright 1987.

(List continued on next page.)

*Primary Examiner*—David C. Nelms
*Assistant Examiner*—John R. Lee
*Attorney, Agent, or Firm*—Fay, Sharpe, Beall, Fagan, Minnich & McKee

[57] ABSTRACT

An engineered lighting system for high speed video inspection includes an array of light emitting diodes including light emitting diodes for use in time delay integration (TDI) inspection of web materials. The light emitting diodes of the array are selectively controllable to accomplish sequential illumination and carefully controllable imaging of a specified section of a continuously moving specimen or specimens. The system also includes an array of optional backlighting elements to aid in illumination of semi-opaque specimens to accomplish inspection thereof.

27 Claims, 5 Drawing Sheets

U.S. PATENT DOCUMENTS

| | | | |
|---|---|---|---|
| 4,604,648 | 8/1986 | Kley | 358/101 |
| 4,606,635 | 8/1986 | Miyazawa et al. | 356/240 |
| 4,677,473 | 6/1987 | Okamoto | 358/101 |
| 4,731,649 | 3/1988 | Chang et al. | 358/106 |
| 4,758,084 | 7/1988 | Tokumi et al. | 356/237 |
| 4,764,681 | 8/1988 | Michalski et al. | 250/563 |
| 4,811,251 | 3/1989 | Minato | 364/552 |
| 4,843,231 | 6/1989 | Caloyannis et al. | 250/223 B |
| 4,860,096 | 8/1989 | Long et al. | 358/101 |
| 4,865,447 | 9/1989 | Shay | 356/240 |
| 4,893,223 | 1/1990 | Arnold | 362/252 |
| 4,922,337 | 5/1990 | Hunt et al. | 358/101 |
| 4,949,172 | 8/1990 | Hunt et al. | 358/101 |
| 5,040,057 | 8/1991 | Gilblom et al. | 358/101 |
| 5,060,065 | 10/1991 | Wasserman | 358/106 |

OTHER PUBLICATIONS

G. Wagner, "Combining X-Ray Imaging and Machine Vision", Penn Video Inc., copyright 1987.

Vinarub, E. J., et al., "Fiber Optics in Machine Vision", Photonics Spectra (Jun., 1987).

Schreiber, Rita R., "Quality Control with Vision", Vision MVA/SME's Quarterly on Vision Technology, vol. 2, No. 4 (Oct. 1985).

George, Robert W., "High Speed Video Inspection of Caps and Closures", Vision '85 Conference Proceedings, pp. 1-55 through 1-70 (Mar. 25-28, 1985).

Strobe Head for Zapata Industries, Inc. Crown Inspection System.

VideoTek Plastic Closure System Inspection System.

ENGINEERED LIGHTING SYSTEM FOR TDI INSPECTION COMPRISING MEANS FOR CONTROLLING LIGHTING ELEMENTS IN ACCORDANCE WITH SPECIMEN DISPLACEMENT

BACKGROUND OF THE INVENTION

This application pertains to the art of machine vision and more particularly to high speed automated video inspection. The invention is particularly applicable to automated video inspection of continuous web-like materials such as cloth, paper, MYLAR, sheet metal, etc., and will be described with particular reference thereto, although it will be appreciated that the invention has broader applications such as in the inspection of any continuously moving specimen whether discrete or continuous in which the specimen passes through the field of view of an associated inspection camera and in systems utilizing relatively low illumination levels.

Machine vision systems have obtained an established presence in industry to accomplish high speed video inspections. Such machine vision systems are generally comprised of a lighting system to illuminate a specimen and a camera for sensing light reflected therefrom. A digitized image is formed from an image received by the camera. Data representative of this image is then utilized for determining acceptability of the specimen in view of preselected physical characteristics thereof.

Earlier array video inspection systems were typically geared to inspection of a continuous sequence of generally uniform specimens which could be contained within the field of view of the inspecting camera. These systems employed lighting which was sufficient to allow for a single illumination period. Still other earlier systems employed indexed cameras which are progressively incremented relative to subportion of a large, usually planar, specimen to obtain a series of images thereof.

Substantial product is manufactured as a continuous stream of webbed or sheet-like material. While the aforementioned systems are adequate for a number of inspections, they provide no means for acquiring a consistently detailed inspection image of a continuous stream of fast moving web material. Earlier attempts to achieve automated inspection of such materials relied upon line scan cameras with continuous illumination. Stroboscopic systems were also utilized but required intense illumination periods. It was therefore desirable that a system be provided which allows for detailed high speed video inspection on a continuous stream of web material or which utilizes heretofore inadequate lighting intensities with improved image integrity and which exhibits robustness over a wide range of specimens.

More recently, advances in cameras, and particularly charge coupled device ("CCD") cameras, has led to time delay integration ("TDI"), techniques such as described by U.S. Pat. Nos. 4,922,337 and 4,949,172. TDI employs a CCD array in which rows of CCD elements which are arranged perpendicularly in relation to a direction of propagation of a continuous webbing or other specimens. A continuous light source reflects light from a generally linear cross-section of the specimen to a row of CCD elements. The resultant image data on that row is shifted to a subsequent, parallel row of elements in the CCD array, whereat additional light flux reflected from the same cross-section of the specimen is integrated therewith. Accordingly, low-light influence due to a single cross-section of the specimen is repeatedly obtained. The resulting combined image averages away substantial noise constituents providing an improved signal-to-noise ratio in a captured image. This allows for obtaining a continuous series of high integrity linear images across the webbing or other specimens.

While the aforementioned TDI technique provides a substantial improvement, it nonetheless presents certain disadvantages. As with more conventional video inspection systems, TDI inspection techniques center on numeric processing, rather than lighting technique. Previous techniques are conducive to some "smearing" of each linear cross-section image. Also, often times different grades of webbing or even entirely different webbing materials may at various times be inspected by the same system. Similarly, non-webbing systems often encounter markedly different specimens at different times. Differences in reflectivity in these situations require compensation. This is typically accomplished by compensation in the inspection algorithm software. Even this is limited given that absolute light sensitivity limits are inherent in CCDs, and once a sensitivity threshold has been exceeded, information is lost and compensation is not possible.

It is also possible to vary lighting intensity, with conventional lighting, however color temperature shifts inherent with incandescent sources and stringent frequency or current controls to effect modification of fluorescent sources are difficult and expensive.

The present invention contemplates a new and improved TDI video inspection and engineered lighting system which overcomes all the above-referred problems, and others, and provides a video inspection system allowing for continuous inspection of a stream of web materials or other specimens with improved integrity.

SUMMARY OF THE INVENTION

In accordance with the present invention, an engineered lighting video inspection system includes an array of light emitting elements. The light emitting elements of the array are secured such that they are controllable in one or more discrete subsets. A signal representative of a linear velocity of an associated specimen relative to the array is provided to a controller. The controller, in turn, functions to selectively enable the light emitting element for a short time period. Light of the array of light emitting elements is, after exposure to the specimen, communicated to a light sensitive transducer array, the rows of which are synchronized to a continuous webbing material or other specimen.

In accordance with yet another aspect of the present invention, backlighting is provided by a plurality of lighting elements disposed on a side of the specimen opposite of the light sensitive transducer.

An advantage of the present invention is the provision of a video inspection system for accomplishing detailed inspection of a continuous stream of sheet or web-like materials or other specimens.

Another advantage of the present invention is the provision of a system which allows for obtaining a frozen image of sequential areas of the web material.

Yet another advantage of the present invention is the provision of a system which allows for accumulation of multiple image data sets from selected areas of a continuous stream of web materials to accomplish improved high speed, detailed video inspection thereof with relatively low light levels, in a system adaptable to a wide range of webbing materials.

Yet another advantage is the provision of an inspection system which achieves an improved signal-to-noise ratio for captured images.

Yet another advantage is the provision of an inspection system employing lighting having improved characteristics, consistency, stability and reliability.

Further advantages will become apparent to one of ordinary skill in the art upon reading and understanding the subject specification.

BRIEF DESCRIPTION OF THE DRAWINGS

The invention may take physical form in certain parts and arrangements of parts, preferred and alternate embodiments of which will be described in detail in the specification and illustrated in the accompanying drawings which form a part hereof and wherein.

DETAILED DESCRIPTION OF THE PREFERRED AND ALTERNATE EMBODIMENT

Figure 1:
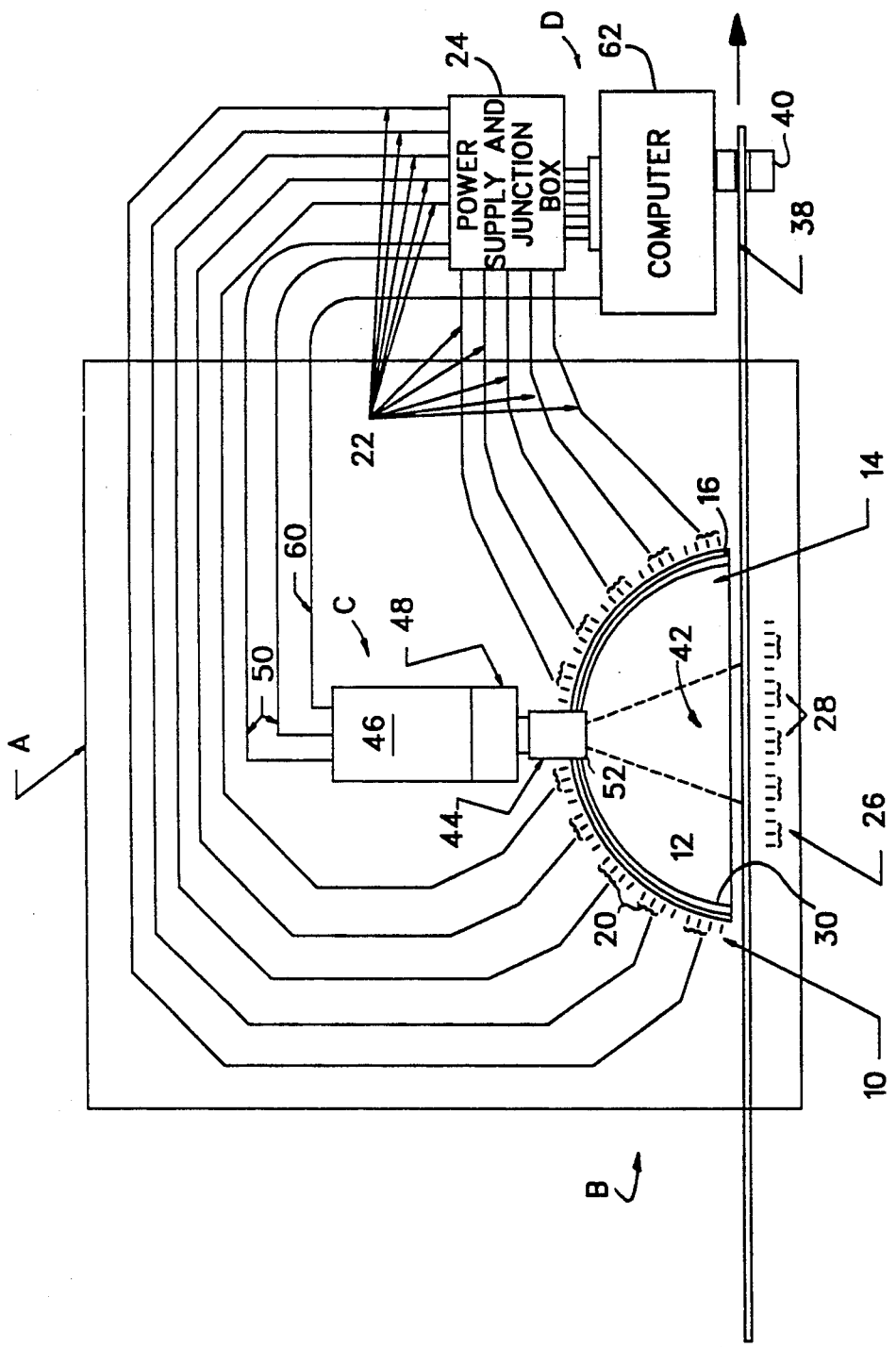
FIG. 1 illustrates a video inspection system employing an array of light emitting diodes.

Referring now to the drawings, wherein the showings are for the purpose of illustrating the preferred and alternate embodiments of the invention only and not for the purposes of limiting the same, FIG. 1 illustrates an engineered video inspection system A which includes an engineered illumination system or means B, a data acquisition system or means C, and a computer system or means D.

The illumination system B is formed from an array of a plurality of light emitting elements 10 preferably comprised of solid-state lighting elements, such as a plurality of light emitting diodes ("LEDs"). Light emitting diodes advantageously provide a fast responsive, long lived, and consistent light output.

Present solid-state light generating elements are available in colors ranging from infrared to blue. Each has distinct advantages for illumination. Selection of wavelength or wavelengths of light vary in conjunction with the selected inspection. Additional consideration is merited by the proportion of illumination energy to the color of light as dictated by $E = h\nu$, where $E$ = energy, $\nu$ = frequency of light, and $h$ = Planck's constant. Earlier LED inspection systems typically employed infrared or red elements given this frequency/energy relationship and the necessity of providing large quantities of light to overcome a short exposure time. Steady-state lighting TDI integrated over a period of time inspections require substantially less light per illumination, thereby rendering possible illumination by various frequency combinations. Repeated, integrated, lighting exposure/image capture sequences allow for use of green, or even blue LEDs notwithstanding their lower efficiency of output. Also, mixed spectra are advantageously implemented to specific inspections. Influences due to multiple light frequencies provide three-dimensional information, as well as a means by which various colors of specimens are inspectable. Multiple cameras are suitably implemented with sensitivity to selected spectrum to isolate various spectral influences. Selected charge-coupled-device ("CCD"), arrays, filters or splitters are suitably implemented to accomplish this.

In the preferred embodiment, the light emitting diodes are focused to a generally narrow beam or cone of light emanating therefrom, which cone has a generally selected angle. However, a similar effect to a focused LEDs may realized by employing a wider beam coupled with a decreased distance between the LEDs and a specimen.

Typical, focused, light emitting diodes include a bullet-shaped casing which functions as a lens to project the narrow beam or cone of light therefrom. What focus is used, the arrangement of the devices, and the angles of illumination chosen is extremely application dependent. Conventionally available focused light emitting diodes have a beam of light generally wide angle (20° at the vertex), or 10° from a perpendicular centerline thereof. The subject system employs selection of LED angles which are highly application dependent. The more focused LEDs allow for concentration of a maximum amount of light from a given LED in a small area while concurrently maintaining uniformity in illumination. This also provides for a higher intensity of illumination on a specified area, subjecting the area to individual controllability of intensities and angles thereacross to controllability of individual or groups or subsets of light emitting diodes.

Light emitting diodes may be pulsed at extremely high currents provided that the duration is sufficiently small to prevent heat build-up which may damage the PN junction forming the diode. It is found that a duration in the range of 1 to 200 microseconds allows for provisions of such high currents with no or nominal damage to the LED. As will be described further below, it will be seen that this duration is also sufficient to "freeze" the image of a rapidly moving specimen so that a still image may be captured therefrom. In the preferred embodiment, 240 scan lines are implemented in the CCD array. Accordingly, 240 pulses and 240 exposures are integrated for each linear cross section of a specimen.

The subject system concurrently flashes all or some of the diodes 10 in a duration of approximately 4 $\mu$sec given the light accumulation properties of TDI. However, operation in the range of 0.1 $\mu$sec to 100 $\mu$sec returns most advantages associated with the subject system. Each LED is suitably supplied with between 1 mA and 500 Ma of current during this duration. A value of 73 Ma has proven acceptable. Suitable power supplies to accomplish such pulsing are well within the understanding of one of ordinary skill in the art and will not be described herein. The 4 $\mu$sec time is selected to advantageously provide low duty cycle compared to the typical horizontal scan time for NTSC video signals. A 15.75 Khz scan rate provides a 63 $\mu$sec horizontal scan time. Accordingly, the 4 $\mu$sec pulse provides a 4/63 duty cycle. This particular rate with actual duty cycle is proportioned to a scan rate implemented for a particular application.

In the embodiment of FIG. 1, the light emitting diodes 10 are secured by a bracket or securing means 12 in a generally hemi-cylindrical array 16. Such an array structure advantageously provides generally uniform illumination to a rectangular light field 14. This structure is suitably fabricated from a flexible printed circuit board portion secured to two hemispherical printed circuit board end portions. LEDs are mounted on the interior portion of the array 16, and are preferably placed as closely as possible to one another to maximize illumination and minimize transitions therebetween, thereby forming a more uniform light field. Although this particular structure is employed in the preferred embodiment, it will be appreciated that various other array structures may be employed for illumination of various specimens.

Angled lighting, i.e., lighting which communicated from one or more LEDS to a specimen and is reflected off the specimen surface to a camera with a stated angle at less than 180°, is advantageously employed for improved detection of certain surface defects. Such systems may optionally implement a perspective correcting lens to maintain image characteristics through the progression within the CCD array. Such a perspective correcting lens allows for direction of light from an array to a specimen at a non-perpendicular angle while negating artifacts which would otherwise result from such an orientation. For example, angled (nonperpendicular) light from a rectangular array which illuminates a specimen causes a trapezoidal illumination area. Moreover, the video receptor of the resultant image is similarly distorted. The reflected image of the lens itself can thus be eliminated by use of a perspective correcting lens when highly reflective materials are being inspected thus allowing the desired degree of homogeneity in the imaged web.

The light emitting diodes 10 are also suitably subdivided into a plurality of groups or subsets 20. Light emitting diodes of each of the subsets 20 are controlled together via connections 22 with a power supply and junction box 24. Grouping of the light emitting elements provides a means with which control of the intensity along selected subsections of an associated specimen may be made or by which selected angles of illumination may be provided. Such structure also provides an ability to compensate for degrading or burned-out elements by boosting output of surrounding elements. It further provides for reduction of reflected light reaching any given region of the camera sensor.

As illustrated in FIG. 1, a portion of the light emitting elements 10 is formed into a backlight array 26. Backlighting is often advantageously employed for inspection of light transmissive specimens or subportions of specimens. In the illustrated embodiment, the backlight array 26 is secured so as to be generally planar. Such a planar orientation is generally best suited for backlighting applications, although it will be appreciated that various other orientations may be successfully utilized. As with lights of the primary array portion 16, light emitting diodes of the backlight array 26 are suitably formed into a plurality of subsets 28, interconnected with power supply and junction box 24. These connections have been omitted from FIG. 1 for ease in illustration. Such formation of subsets provides for controllability analogous to that provided with the arrangement above-described for primary array portion 16.

Illustrated in FIG. 1 is a cross-sectional side view of a diffuser 30. The diffuser 30 is advantageously formed as a hemi-cylindrical shape to be similar to the shape of the array 16, and placed internally thereof. The optional diffuser functions to smooth transitions between LEDs of the array, thereby providing an even more uniform light field.

Also illustrated in FIG. 1 is segment 38 of a stream of webbing material which is in generally continuous motion in the direction so indicated. Again, as used herein, webbing material will be understood to refer to any sheetlike material, such as paper, cloth, sheet metal, plastic, laminates, and the like. It is understood that the system is also advantageously employed in discrete specimen systems. However, for simplicity descriptions herein will generally be with sole reference to webbing environments. A conveyor driver (not shown) continuously moves the web 38 through the light field 14 at a generally high speed. Web position is measured by a web position/velocity sensor, such as a tachometer 40. Light from light emitting diodes 10 of the primary array portion 16 is reflected from the web 38. Reflected light from a viewing area 42 is received through a lens 44 of a camera 46. Although only one camera is illustrated in the cross-sectional view of the figure, it will be shown below that often a plurality of cameras are advantageously employed. The viewing area 42 is isolated as much as possible from ambient light, i.e., light not provided by light from the primary (or secondary) lighting array(s) 16 (28).

In the embodiment of FIG. 1, the lens 44 of camera 46 is secured to extend slightly into the light field 14 through an aperture portion 52. The lens 44 is preferably formed as a "pinhole" unit to minimize image artifacts due to the camera itself. Such lens arrangements are typically less than ⅜" in diameter. In a symmetrical array such as the hemi-cylindrical primary array portion 16, the aperture portion is suitably disposed at a generally central portion of the array should one camera be utilized, and at equivalent intervals in embodiments employing a plurality of cameras. The subject system, in its preferred embodiment, employs a TDI camera, VISIONEER 4050 manufactured by Picker International, Inc.

The camera 46 includes a CCD array in the preferred embodiment. It will be appreciated that CCD arrays are usually $M \times N$ rectangular arrays of photosensitive transducer elements, wherein M and N are positive, non-zero integers, usually multiples of two. The camera of the preferred embodiment functions as 244 rows of CCD elements, each row having 610 pixels.

In the arrangement of FIG. 1, the camera 46 is oriented relative to the web 40 such that each row is generally perpendicular to the direction of travel thereof. Typical CCD arrays are sensitive to a selected number of gray scale levels, for black and white systems, or primary colors, for color systems.

Commonly available CCD cameras allow for individual addressing of rows of transducer element thereof, analogously to the raster scan associated with conventional cathode ray tubes ("CRTs"). CCD elements also operate as integrators which provide an electrical signal representative of an intensity of light exposed thereto over time. A CCD transducer element also has the ability to store light intensity data. This property is useful for achieving a still image of a specimen or portion thereof by strobing or pulsing a light source when the moving specimen is otherwise in a generally darkened field of view.

The camera 46 also advantageously includes an adjustment system 48 for control of focus, planetary, vertical, horizontal properties. Orthogonality must be maintained between sensor and inspected material. Such adjustment may be done manually, or in conjunction with signals provided by the digital computer system D by data communication camera sync and control lines.

Image data acquired from camera 46 is communicated, through video signal line 60, to the digital computer system D, and more particularly to the computer 62 thereof. The computer 62 includes a central processor (CPU), memory, an I/O unit, and a suitable software and junction box 24 and with the webbing speed sensor 40. The computer 62 determine acceptability of the specimens by a comparison of digitized image data with data representative of acceptability.

Figure 2:
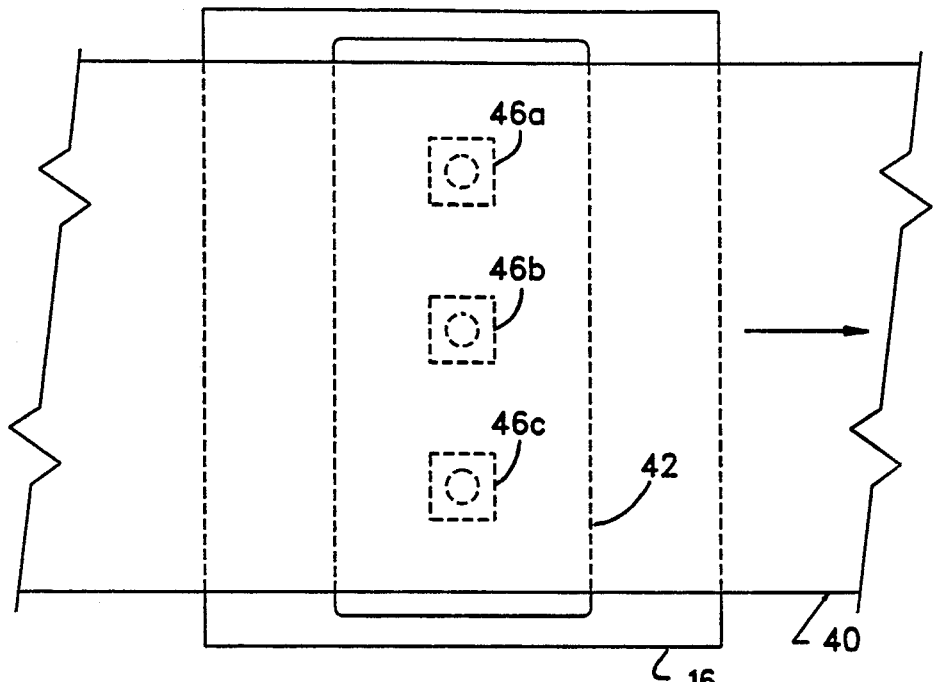
FIG. 2 illustrates an overhead view of three cameras positioned to accomplish image acquisition for inspection of webbing material.

Although only one camera is visible in the embodiment of FIG. 1, certain applications are advantageously served by a plurality of cameras. FIG. 2 illustrates an embodiment in which three cameras, 46a, 46b, and 46c are oriented relative to webbing material 38 in a mutual linear relationship. Respective viewing areas of the cameras are linearly aligned to provided a cross-section of the entire specimen surface. Securing the cameras in this manner provides an extended viewing area 42 sufficient to encompass a cross-section of a relatively wide webbing.

Figure 3:
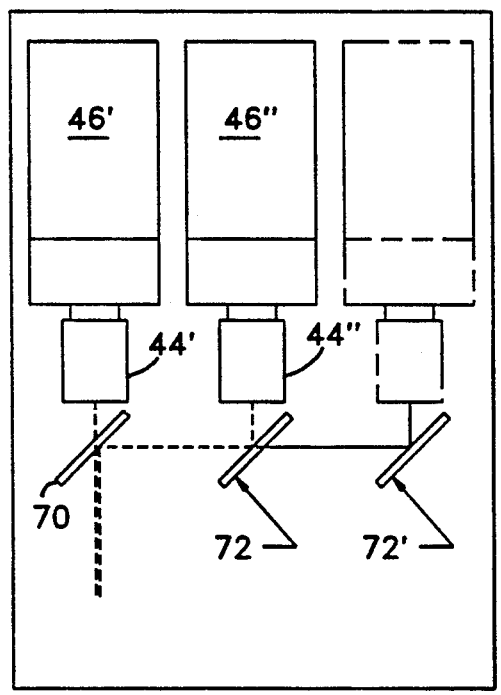
FIG. 3 illustrates an optional dual-camera inspection embodiment.

FIG. 3 illustrates an embodiment in which camera 46 is itself formed from a plurality of cameras. In this embodiment, light from a specimen is communicated to a partially silvered mirror 70. A portion passes directly to lens 44' of camera 46'. A second light portion is reflected from mirror 72 to lens 44" of camera 46". Implementation of a dual or multiple camera structure, such as that illustrated by FIG. 3, advantageously provides a means by which selected portions of the specimen may be provided with either increased resolution to accomplish specialized inspections or optical filtering thereon. For example, a seam or scoring in the inspected web material might be subject to heightened scrutiny by virtue of utilization of a secondary camera element focused specifically thereon. Similarly, a third camera is also advantageously implemented for additional subportion analysis, as illustrated in phantom as numeral 72' in FIG. 3. Lighting to of such multiple camera beam-splitter environments will generally not yield as desirable a result or design because of the intense lighting required to provide enough light to each camera (when the exposure time is short and) since the splitting reduces the intensity inherently.

It will be appreciated that certain application may employ multiple two-camera or three-camera modules, for example, disposed as illustrated by FIG. 2 with suitable magnification and clock speeds.

Figure 4:
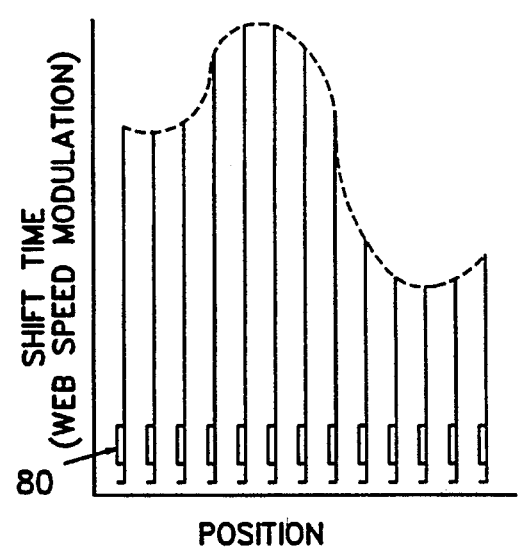
FIG. 4 is a graph of shift time versus position for an inspection of a continuous moving stream of webbing material.
Figure 5:
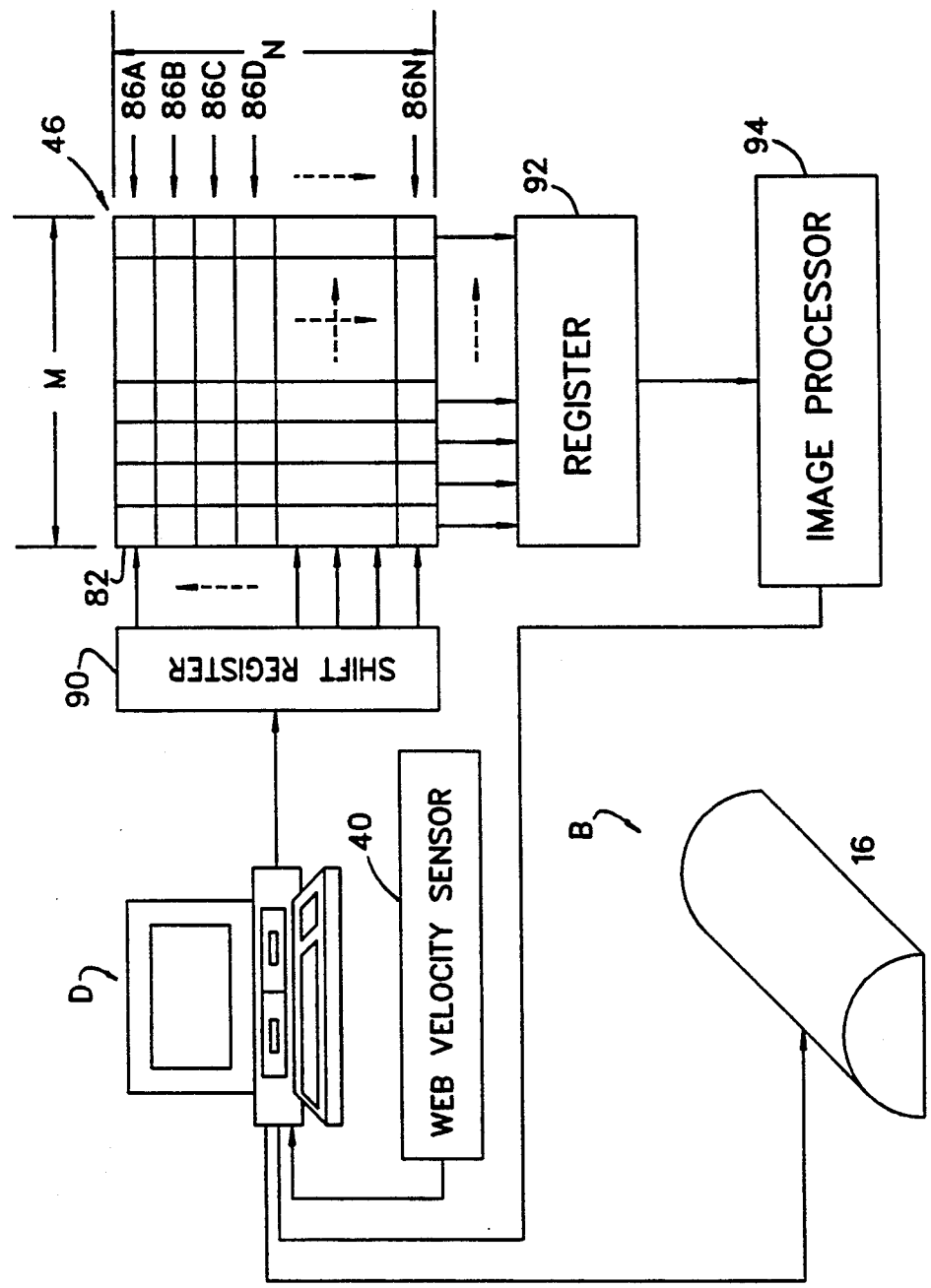
FIG. 5 illustrates the illumination and CCD subsystems employed in the system of FIG. 1.

Turning now to FIGS. 4 and 5, a graph illustrating operation of the charge coupled devices within the camera or cameras 46 is provided. In the illustrated graph, position is represented by the abscissa while shift time is represented by the ordinate. It will be recalled from the discussion above concerning CCDs that light sensitive transducers elements thereof are arranged in an M ×N grid. Data in each row of CCD elements is typically sequentially accessed and read in a raster-type fashion. This property is seized upon to accomplish a sequence of linear scans from a plurality of linear cross-sections of the webbing specimen surface. Accessing of scan lines of the CCD array is advantageously synchronized with the velocity of webbing material 38. When non-continuous lighting is chosen, a series of illuminations or light pulses are represented by the rectangles 80 of the graph. In the event multiple cameras are used, rows or scan lines of each are preferably synchronized between all cameras. It is also equivalent to provide multiple pulses per scan line if advantageous.

Synchronization between the CCD and the webbing may be accomplished by control of web velocity or of CCD row increments. In the preferred embodiment, the CCD row incrementing is altered in accordance with variations in web speed by variations in shift control as described below.

With particular reference to FIG. 5, orientation of a CCD array 82 is provided. The digital computer system D, which is illustrated with a keyboard, CRT, and mass storage media, and which includes the computer 62, receives a signal representative of web velocity from a sensor 40. This information is in turn utilized to sequence the scan of row 86 of a CCD array elements 88, via row scan selected circuitry illustrated as shift register 90. Similar sequencing is provided for each CCD array in multiple camera embodiments. The webbing progression is continuously monitored and the shift time implemented by the row select circuitry 90 is altered in accordance therewith. The graph of FIG. 4 illustrates the variation and shift time in accordance with the web speed.

Figure 6:
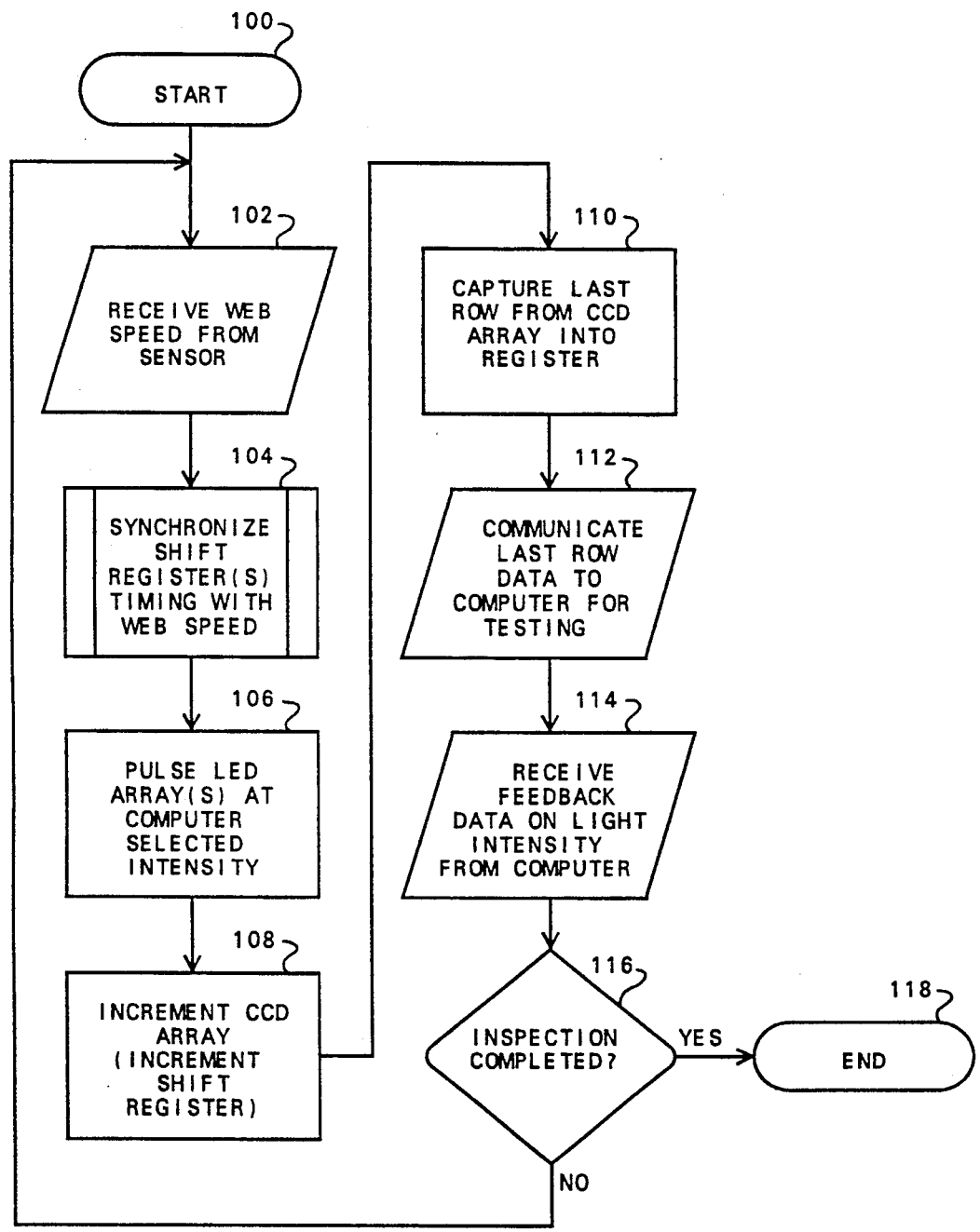
FIG. 6 illustrates a flow chart of operation of the subject TDI engineered lighting inspection operation.

Turning now to FIG. 6, a flow chart illustrating operation of the subject TDI illumination process will be described. The operation commences at start step 100 and progresses to I/O step 102. At step 102, data representative of web speed is obtained from tachometer 40. In step 104, web speed data is utilized to synchronize the shift register or registers of the CCD cameras with the web speed velocity data obtained in step 102. In step 106, the array or arrays of LEDs is pulsed for a short duration, approximately 4 $\mu$sec. in the preferred embodiment as noted above. This duration, by virtue of the synchronization with the webbing speed, is timed at the point when the previous shifting operation has settled, thereby providing the minimized smearing. Lighting intensity is also alterable in connection with this step.

At step 108, the digital computer instructs shifting of shift register 90 to cause progression of rows of the CCD array 82 towards register 92. Accordingly, at this time the contents of previous row 86N are then communicated to register 92 in step 110. This data is, in turn, communicated through image processor 94 to digital computer system D at step 112. At this stage, a suitable algorithm is performed on the data to determine acceptability of the specimen.

At step 114, lighting intensity adjustment data is received to allow for selective control of intensity in step 106. Step 116 allows completed inspections to terminate at step 118 and continuing inspections to progress back to step 102.

Figure 7:
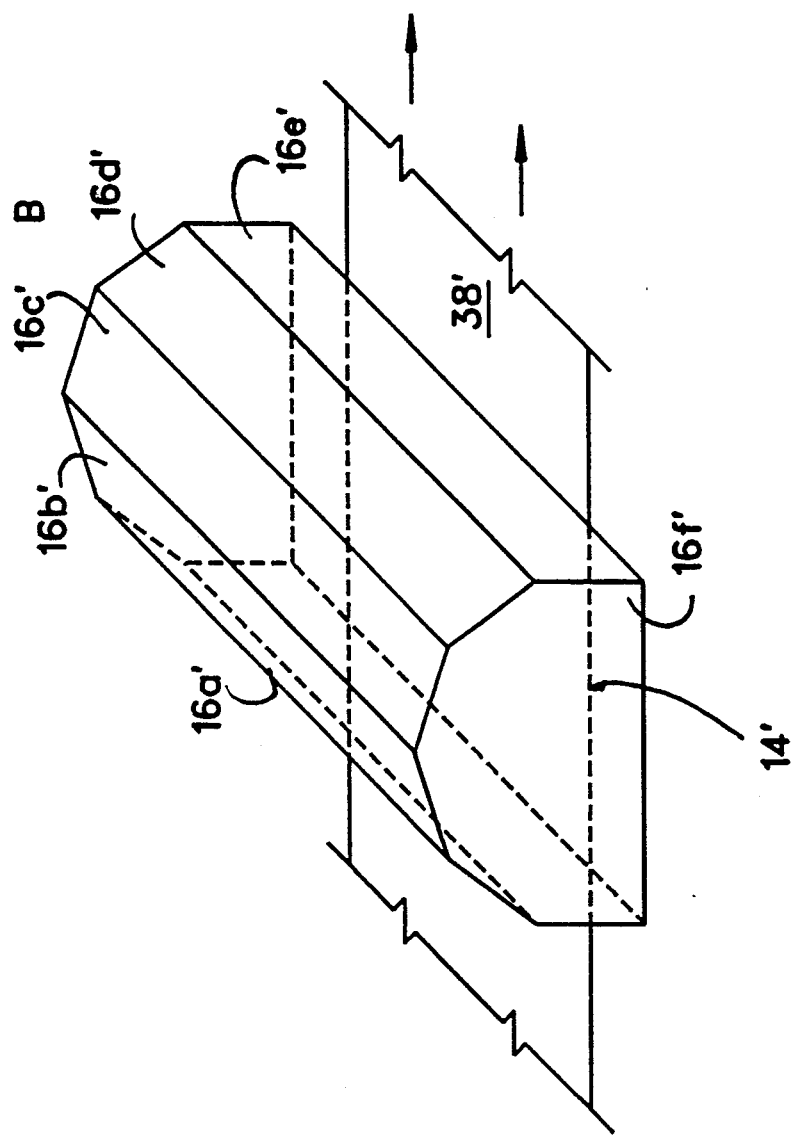
FIG. 7 is an alternate embodiment of the primary lighting array illustrated in FIGS. 1 and 5.

FIG. 7 illustrates an alternative embodiment of the primary array 16 illustrated in FIGS. 1 and 5. In this embodiment, the primary array 16' is formed from a series of planar rectangular portions 16a'-16d' and first and second planar end portions 16e' and 16f'. As with the hemicylindrical array illustrated in FIGS. 1 and 5, an interior portion of the array 16' contains closely packed LEDs directed to the webbing material 38'. This embodiment advantageously allows for fabrication of the array 16' from common, planar printed circuit board material. This orientation nonetheless provides for substantial uniform illumination over a light field 14' which encompasses a portion of the webbing 38'. It will be appreciated that more or fewer rectangular subsections may be utilized depending on the degree to which a hemispherical array is more closely advantageously approximated. Further array formats may also be utilized, which formats are dictated by properties or dimensions of the webbing material and the angles and intensities of illumination required to provide the desired qualities of the illumination. For example, hemispherical, "tiffany-lamp" style, etc. or otherwise may be utilized.

The modulated row select CCD structure provides a system with which multiple readings of a single linear subsection of a continuously moving web material may be achieved without the necessity of using a plurality of cameras or a moving camera. Data achieved by multiple acquisition provides more reliable data upon which inspection may be made. Also lighting specific to subsections of the CCD may be advantageously applied at appropriate angles and intensities.

The invention has been described with reference to the preferred and alternate embodiments. Obviously, modifications and alterations will occur to others upon a reading and understanding of this specification. It is intended that all such modifications and alterations be included insofar as they come within the scope of the appended claims or the equivalents thereof.

Having thus described our invention, we now claim:

1. A engineered video inspection illumination system comprising:
   a first array of light emitting diodes;
   first securing means adapted for securing the first array such that light emanating from each light emitting diode thereof is directed to an associated specimen disposed in an illumination region such that lighting intensity on a selected portion of a surface of the associated specimen is primarily attributable to a selected subset of the light emitting diodes;
   means for receiving a displacement signal representative of a linear displacement of the associated specimen relative to the first array over a selected scan period;
   controller means for selectively supplying a current pulse to the light emitting diodes during the scan period in accordance with the displacement signal such that each of a plurality of generally linear sections of the associated specimen is illuminated a plurality of times by the light emitting diodes; and
   means for communicating the displacement signal to the controller means.

2. The engineered video inspection illumination system of claim 1 wherein the controller means includes means for supplying a current pulse to the light emitting diodes for each scan line of an associated charge coupled device array.

3. The engineered video inspection illumination system of claim 2 wherein the light emitting diodes provide light in the visible spectrum.

4. The engineered video inspection illumination system of claim 2 wherein the means for receiving a displacement signal includes means for receiving a displacement signal representative of a speed of a generally continuous specimen, a length of which substantially exceeds the illumination region.

5. The engineered video inspection illumination system of claim 4 wherein the controller means includes means for supplying the current pulse with a duration in the range of 0.1 microsecond to 100 microseconds.

6. The engineered video inspection illumination system of claim 5 wherein the controller means includes means for supplying the current pulse with a duration in the range of 1 microsecond to 10 microseconds.

7. The engineered video inspection illumination system of claim 6 further comprising means for masking a portion the associated specimen disposed within the illumination region from at least one of ambient light and light of a selected wavelength.

8. The engineered video inspection illumination system of claim 7 wherein the first securing means further includes means for securing the first array of light emitting diodes into an interior of a generally hemicylindrical orientation.

9. The engineered video inspection illumination system of claim 8 further comprising:
   a second array of light emitting diodes;
   second securing means for securing the second array of light emitting diodes such that at least a portion of light directed therefrom is directed generally toward the light emitting diodes of the first array after refraction thereof through the associated specimen.

10. The engineered video inspection illumination system of claim 9 wherein the second securing means includes means for securing the second array of light emitting diodes into a generally planar orientation.

11. A engineered video inspection system comprising:
    an array of light emitting diodes;
    means adapted for securing the array of light emitting diodes such that light emitted therefrom is directed to a portion of a generally continuously moving associated specimen;
    means for receiving a displacement signal representative of a speed of the associated specimen relative to the array over a selected scan period;
    controller means for selectively supplying a current pulse to selected light emitting diodes of the array in accordance with the displacement signal during the scan period such that a portion of the associated specimen is sequentially illuminated by a plurality of the rows of light emitting diodes of the array;
    means for communicating the displacement signal to the controller means; and
    an array of light sensitive transducer elements adapted to receive light generated by the array of light emitting diodes after exposure to the associated specimen.

12. The engineered video inspection system of claim 11 wherein the array of light sensitive transducer elements is formed as a plurality of generally parallel rows secured to be generally perpendicular to a direction of propagation of the associated specimen, and wherein the array of light sensitive transducer elements includes selection means for selectively addressing individual rows thereof such that data representative of a previous exposure stored in a selected row of light generating elements is periodically communicated to a neighboring row of transducer elements.

13. The engineered video inspection system of claim 12 wherein the means for receiving the displacement signal includes means for receiving the displacement signal representative of a linear speed of a generally continuous stream of webbing material, and wherein the selection means includes means for selectively addressing the individual rows of the light emitting diodes of the array so as to successively illuminate a generally equivalent linear portion of the webbing material by successive control of the selective addressing.

14. The engineered video inspection system of claim 13 wherein the light emitting diodes provide light in the visible spectrum.

15. An engineered lighting video inspection system comprising:
an array of light emitting elements;
securing means adapted for securing the array into a plurality of lighting element subsets of light emitting elements such that a cone of light emanating from each lighting element subset is directed to a selected region of an associated specimen;
means for receiving a displacement signal representative of a linear velocity of the associated specimen relative to the array;
controller means for selectively controlling effective intensity of each of the lighting element subsets in accordance with the displacement signal during a scan period such that a single portion of the associated specimen is sequentially illuminated by discrete lighting element subsets;
means for communicating the displacement signal to the controller means;
an array of light sensitive transducer elements adapted to receive light generated by the array of focussed light emitting elements after exposure to the associated specimen;
wherein the array of light sensitive transducer elements is formed as a plurality of transducer element subsets, and wherein the array of light sensitive transducer elements includes selection means for selectively addressing individual transducer element subsets thereof, the selection means including means for sequentially addressing selected discrete transducer element subsets which correspond to each of the discrete lighting element subsets so as to repetitively illuminate a generally equivalent portion of the associated specimen successively.

16. The engineered lighting video inspection system of claim 15 wherein the securing means further includes means for securing each light emitting element subset as a plurality of generally parallel rows.

17. The engineered video inspection system of claim 16 wherein the light emitting elements provide light in the visible spectrum.

18. A video inspection method comprising the steps of:
receiving a displacement signal representative of a linear displacement of an associated specimen relative to an array of a plurality of generally parallel rows of focussed light emitting diodes disposed such that a cone of light emanating from diodes of each row of light emitting diodes is directed to a generally linear region of an associated specimen over a selected scan period;
selectively controlling effective intensity of each of the rows of light emitting diodes in accordance with the displacement signal during the scan period such that a single portion of the associated specimen is sequentially illuminated by a plurality of the rows of light emitting diodes of the array; and
receiving light generated by the light emitting diodes into a plurality of transducer elements adapted to receive light generated by the array of focussed light emitting elements after exposure to the associated specimen.

19. The method of claim 18 further comprising the step of selectively addressing individual rows of the plurality of rows of light emitting diodes.

20. The method of claim 19 further comprising the steps of:
receiving the displacement signal representative of a linear speed of a generally continuous stream of webbing material; and
selectively addressing the individual rows so as to successively illuminate a generally equivalent linear portion of the webbing material by successive control of the selective addressing.

21. The engineered video inspection system of claim 20 wherein the light emitting diodes provide light in the visible spectrum.

22. A engineered video inspection system comprising:
a first array of light emitting diodes;
first securing means adapted to illuminate an associated specimen disposed in an illumination region such that lighting intensity on a selected portion of a surface of the associated specimen is primarily attributable to a selected subset of the light emitting diodes;
means for receiving a displacement signal representative of a linear displacement of the associated specimen relative to the first array over a selected scan period;
means for supplying current to the light emitting diodes in accordance with the displacement signal during the scan period such that the selected portion is illuminated a plurality of times;
video receptor means for synchronously integrating a plurality of images of the associated specimen, which images result from exposure of the associated specimen to light of the first array; and
means for communicating the displacement signal to the video receptor to synchronize the video receptor with the linear displacement of the associated specimen relative to the first array.

23. The engineered video inspection illumination system of claim 22 wherein the means for receiving a displacement signal includes means for receiving a displacement signal representative of a speed of each of a stream of discrete specimens.

24. The engineered video inspection system of claim 23 wherein the securing means includes means for aligning the light emitting diodes of the first array such that light emanating therefrom is directed to the associated specimen at a selected angle.

25. The engineered video inspection system of claim 24 further comprising a lens means for providing light to the video receptor means after exposure thereof to the associated specimen.

26. The engineered video inspection system of claim 24 wherein the lens means includes a perspective correcting lens.

27. The engineered video inspection system of claim 26 wherein the light emitting diodes provide light in the visible spectrum.

* * * * *